(12) United States Patent  
Takagahara et al.

(10) Patent No.: US 10,799,136 B2  
(45) Date of Patent: Oct. 13, 2020

(54) BIOELECTRODE AND GARMENT

(71) Applicants: NIPPON TELEGRAPH AND TELEPHONE CORPORATION, Tokyo (JP); TORAY INDUSTRIES, INC., Tokyo (JP)

(72) Inventors: Kazuhiko Takagahara, Tokyo (JP); Ryusuke Kawano, Tokyo (JP); Takako Ishihara, Tokyo (JP); Michiko Seyama, Tokyo (JP); Ryoichi Kasahara, Tokyo (JP); Yasuhiro Sato, Tokyo (JP); Atsushi Horiuchi, Tokyo (JP); Masanobu Sato, Tokyo (JP); Emiko Ishikawa, Osaka (JP); Keiji Takeda, Shiga (JP); Noriko Nagai, Shiga (JP)

(73) Assignees: NIPPON TELEGRAPH AND TELEPHONE CORPORATION, Tokyo (JP); TORAY INDUSTRIES, INC., Tokyo (JP)

( * ) Notice: Subject to any disclaimer, the term of this patent is extended or adjusted under 35 U.S.C. 154(b) by 509 days.

(21) Appl. No.: 15/533,982

(22) PCT Filed: Dec. 7, 2015

(86) PCT No.: PCT/JP2015/084270  
§ 371 (c)(1),  
(2) Date: Jun. 7, 2017

(87) PCT Pub. No.: WO2016/093194  
PCT Pub. Date: Jun. 16, 2016

(65) Prior Publication Data  
US 2017/0340226 A1 Nov. 30, 2017

(30) Foreign Application Priority Data

Dec. 8, 2014 (JP) .................................. 2014-247860

(51) Int. Cl.  
*A61B 5/0408* (2006.01)  
*A61B 5/0478* (2006.01)  
(Continued)

(52) U.S. Cl.  
CPC .......... *A61B 5/0408* (2013.01); *A61B 5/0478* (2013.01); *A61B 5/6804* (2013.01);  
(Continued)

(58) Field of Classification Search  
CPC ....... A61B 5/04; A61B 5/0408; A61B 5/0478; A61B 5/68; A61B 5/6801; A61B 5/6802;  
(Continued)

(56) References Cited

U.S. PATENT DOCUMENTS

2007/0285868 A1 12/2007 Lindberg et al.  
2009/0306485 A1 12/2009 Bell  
(Continued)

FOREIGN PATENT DOCUMENTS

CA 2818005 A1 5/2012  
CN 1795815 A 7/2006  
(Continued)

OTHER PUBLICATIONS

Office Action received for Japanese Patent Application No. 2019-700176, dated May 9, 2019, 26 pages (11 pages of English Translation and 15 pages of Office Action).

(Continued)

*Primary Examiner* — Linda C Dvorak  
*Assistant Examiner* — Bradford C. Blaise  
(74) *Attorney, Agent, or Firm* — Womble Bond Dickinson (US) LLP

(57) ABSTRACT

A bioelectrode includes a fitting member (1106) formed by an electrically insulating member fixed on a surface of a garment (1100) that comes in contact with a living body (1000), an electrode part (1101*a*) formed by a conductive (Continued)

member fixed on a surface of the fitting member (1106) that comes in contact with the living body (1000), a connector (1102*a*) fixed to the fitting member (1106) and configured to connect a bioelectric signal measurement device, a wiring line (1103*a*) fixed to the fitting member (1106) and configured to electrically connect the connector (1102*a*) and the electrode part (1101*a*), and an electrically-insulating insulating member (1105) configured to cover a portion within the surface of the wiring line (1103*a*) that comes in contact with the living body (1000).

11 Claims, 7 Drawing Sheets

(51) Int. Cl.
*A61B 5/00* (2006.01)
*A61B 5/04* (2006.01)
*A61N 1/04* (2006.01)

(52) U.S. Cl.
CPC ............ *A61B 5/04* (2013.01); *A61B 5/04085* (2013.01); *A61B 5/6802* (2013.01); *A61N 1/0404* (2013.01); *A61N 1/0472* (2013.01); *A61N 1/0484* (2013.01); *A61N 1/0488* (2013.01)

(58) Field of Classification Search
CPC ... A61B 5/6804; A61B 5/683; A61B 5/04085; A61N 1/04; A61N 1/0404; A61N 1/0484; A61N 1/0488
See application file for complete search history.

(56) References Cited

U.S. PATENT DOCUMENTS

| | | | |
|---|---|---|---|
| 2010/0130846 A1 | 5/2010 | Rytky | |
| 2010/0198038 A1 | 8/2010 | Nagata et al. | |
| 2013/0019383 A1* | 1/2013 | Korkala | A61B 5/6804 2/338 |
| 2013/0041272 A1 | 2/2013 | Guillen et al. | |
| 2013/0131484 A1* | 5/2013 | Pernu | A61B 5/04085 600/388 |
| 2013/0225966 A1* | 8/2013 | Macia Barber | A61B 5/0492 600/388 |
| 2013/0338472 A1 | 12/2013 | Macia Barber et al. | |
| 2014/0343391 A1* | 11/2014 | Korkala | A61B 5/0408 600/393 |
| 2015/0223716 A1* | 8/2015 | Korkala | A61B 5/0245 600/393 |
| 2016/0374615 A1 | 12/2016 | Tsukada et al. | |

FOREIGN PATENT DOCUMENTS

| | | |
|---|---|---|
| CN | 101848675 A | 9/2010 |
| CN | 103930612 A | 7/2014 |
| EP | 1676528 A1 | 5/2006 |
| EP | 2679107 A1 | 1/2014 |
| EP | 2803315 A1 | 11/2014 |
| JP | H02-142534 A | 5/1990 |
| JP | H09-253219 A | 9/1997 |
| JP | 2005-349021 A | 12/2005 |
| JP | 2014-500077 A | 1/2014 |
| JP | 2014-108134 A | 6/2014 |
| WO | 2012/066056 A1 | 5/2012 |
| WO | WO 2014/160848 A | 10/2014 |
| WO | 2015/115441 A1 | 8/2015 |

OTHER PUBLICATIONS

Office Action received for Australian Patent Application No. 2015362507, dated Jul. 18, 2019, 3 pages.
Office Action received for Japanese Patent Application No. 2018-094366, dated Jul. 30, 2019, 7 pages (4 pages of English Translation and 3 pages of Office Action).
Office Action received for Japanese Patent Application No. 2018-094366, dated Mar. 19, 2019, 41 pages (25 pages of English Translation and 16 pages of Office Action).
Office Action received for Canadian Patent Application No. 2969646, dated Jan. 9, 2019, 4 pages.
Ribeiro, et al., "A Real time, Wearable ECG and Continuous Blood Pressure Monitoring System for First Responders", 33rd Annual International Conference of the IEEE EMBS, pp. 6894-6898, 2011.
Office Action received for Japanese Patent Application No. 2019-700176, dated Apr. 11, 2019, 119 pages (75 pages of English Translation and 44 pages of Office Action).
Office Action received for Chinese Patent Application No. 201580066592.X, dated Jul. 26, 2019, 10 pages (4 pages of English Translation and 6 pages of Office Action).
Supplementary European Search Report and Written Opinion received for EP Patent Application No. 15868269.0, dated Jun. 27, 2018, 8 pages.
International Search Report and Written Opinion received for PCT Patent Application No. PCT/JP2015/084270, dated Mar. 1, 2016, 15 pages (8 pages of English Translation and 7 pages of Original Document).
International Preliminary Report on Patentability received for PCT Patent Application No. PCT/JP2015/084270, dated Jun. 22, 2017, 13 pages (8 pages of English Translation and 5 pages of Original Document).
Office Action received for Japanese Patent Application No. 2018-094366, dated Mar. 19, 2019, 6 pages (3 pages of English Translation and 3 pages of Office Action).
Office Action received for EP Patent Application No. 15868269.0, received on Mar. 21, 2019, 3 pages.
Office Action received for Chilean Patent Application No. 2017-001451, dated Nov. 15, 2018, 29 pages (18 pages of English Translation and 11 pages of Office Action).
Office Action received for Japanese Patent Application No. 2019-124307, dated May 26, 2020, 8 pages (4 pages of English Translation and 4 pages of Office Action).

* cited by examiner

BIOELECTRODE AND GARMENT

TECHNICAL FIELD

The present invention relates to a bioelectrode for measuring a bioelectric signal, such as an electrocardiogram, and a garment on which the bioelectrode is fixed.

BACKGROUND ART

A bioelectrode which is attached to the body surface is widely used in order to record bioelectric signals such as a brain wave, event-related potential, evoked potential, myogenic potential, and cardiac potential, and to give electrical stimulation to a living body. Recently, as one individual health management method, a method of recording an electrocardiogram waveform over a long period of time and analyzing changes in waveform is known to be effective in preventive medicine, because the method can find an autonomic disorder and cardiac symptom. To obtain an electrocardiogram waveform over a long period of time, a garment (wearable electrode) on which a bioelectrode is attached is attracting attention (see literature "David M. D. Ribeiro, et al., "A Real time, Wearable ECG and Continuous Blood Pressure Monitoring System for First Responders", 33rd Annual International Conference of the IEEE EMBS, pp. 6894-6898, 2011").

The wearable electrode is generally divided into an electrode part to be brought into contact with a living body, a connector to which a terminal for measuring a bioelectric signal is attached, a wiring line for connecting the electrode part and connector, and a cloth part as a base to which the electrode part, connector, and wiring line are attached. Conductivity is given to only the electrode part, connector, and wiring line, and the cloth part is formed by an electrical insulator. With this configuration, a desired bioelectric signal can be obtained from only the electrode part.

DISCLOSURE OF INVENTION

Problem to be Solved by the Invention

However, in general, a material which absorbs water such as sweat or rain is used as the material of the garment in order to secure comfortableness in use. A garment containing an electrolyte loses its electrical insulation properties. Therefore, if a wearer perspires or when used in rainy weather, the related wearable electrode cannot ensure electrical insulation between the garment and a conductor such as the electrode part, connector, or wiring line. This poses the problems that no desired bioelectric signal can be obtained because a bioelectric signal detected in a garment part other than the electrode part mixes in a bioelectric signal obtained from the electrode part, and that a bioelectric signal deteriorates because a plurality of electrodes electrically short-circuit. Note that rain is originally not an electrolyte, but may function as an electrode due to the influence of acid rain or the like.

The present invention has been made to solve the above problems, and makes it possible to obtain a desired bioelectric signal even when a garment gets wet after a bioelectrode is attached on the garment.

Means of Solution to the Problem

A bioelectrode of the present invention comprises a fitting member formed by an electrically insulating member fixed on a surface of a garment that comes in contact with a living body, an electrode part formed by a conductive member fixed on a surface of the fitting member that comes in contact with a living body, a connector fixed to the fitting member and configured to connect a bioelectric signal measurement device, a wiring line fixed to the fitting member and configured to electrically connect the connector and the electrode part, and an electrically-insulating first insulating member configured to cover a portion of a surface of the wiring line, which comes in contact with a living body.

Effect of the Invention

According to the present invention, the electrode part, connector, and wiring line are attached to the electrically-insulating fitting member, and a portion within the surface of the wiring line that comes in contact with a living body is covered with the electrically-insulating first insulating member. Therefore, even when a garment gets wet after the fitting member is attached on the garment, the present invention is capable of preventing a shortcircuit between the wiring line and a living body, or a shortcircuit between a plurality of electrodes, and obtain a desired bioelectric signal.

BEST MODE FOR CARRYING OUT THE INVENTION

First Embodiment

A wearable electrode (bioelectrode) according to the present invention will be explained in detail below with reference to the accompanying drawings. Note that the present invention is not limited by the following embodiments.

Figure 1:
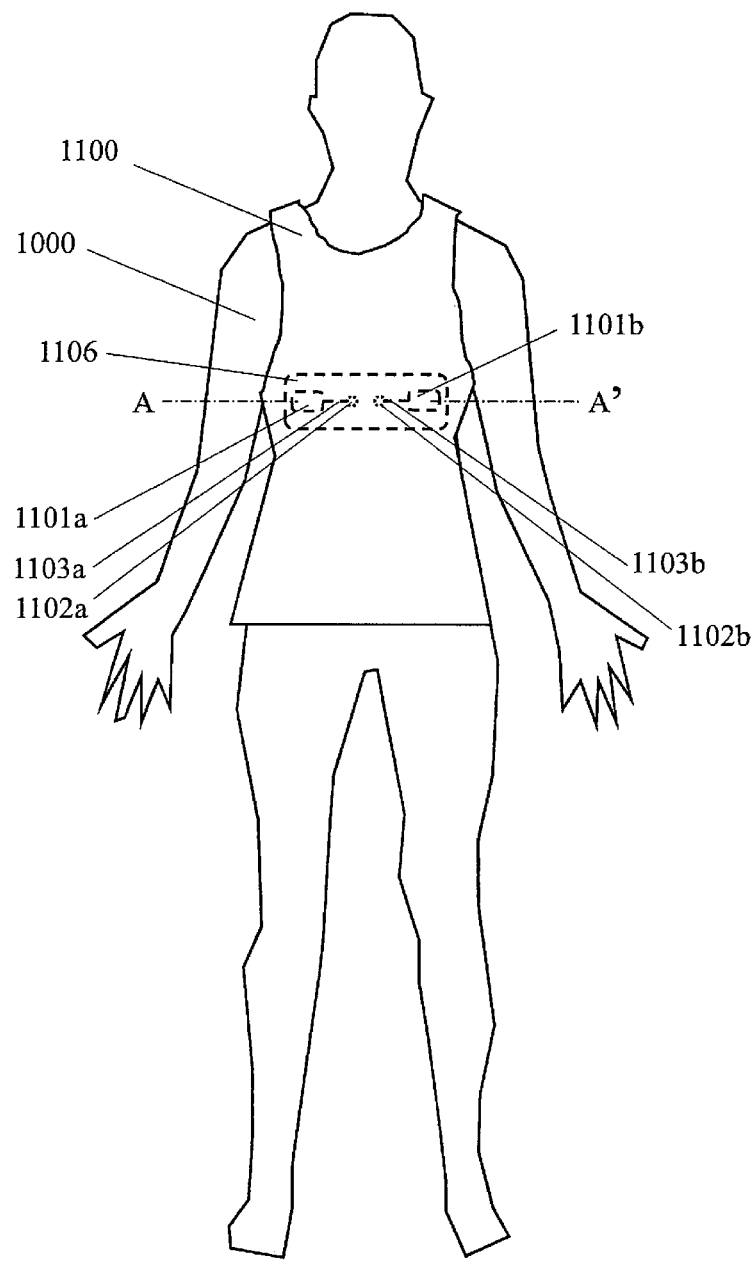
FIG. 1 is a schematic view showing the way a wearable electrode according to the first embodiment of the present invention is worn on a living body.
Figure 2:
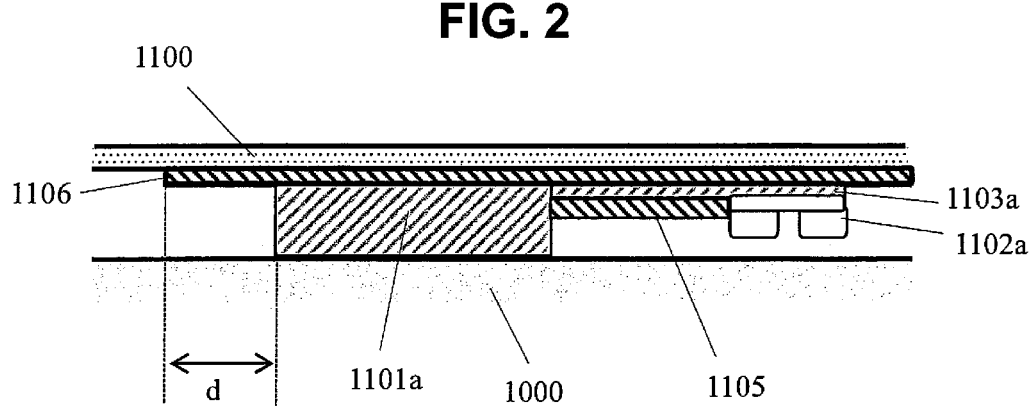
FIG. 2 is a sectional view of the wearable electrode according to the first embodiment of the present invention.

FIG. 1 is a schematic view showing the way a wearable electrode according to the first embodiment of the present invention is worn on a living body. FIG. 2 is an A-A' sectional view of the wearable electrode shown in FIG. 1. Note that FIG. 2 shows only a set of an electrode part, wiring line, and connector.

The wearable electrode of this embodiment includes two electrode parts 1101*a* and 1101*b* formed by conductive fiber structures which come in contact with a living body 1000 (a wearer), connectors 1102*a* and 1102*b* for connecting a bioelectric signal measurement device which detects a bioelectric signal obtained by the electrode parts 1101*a* and 1101*b*, wiring lines 1103*a* and 1103*b* for electrically connecting the electrode parts 1101*a* and 1101*b*, and connectors 1102*a* and 1102*b*, a waterproof electrically-insulating insulating member 1105 for covering those portions of the surfaces of the wiring lines 1103*a* and 1103*b*, which come in contact with the living body 1000, a fitting member 1106 formed by a waterproof electrically insulating member for fixing the electrode parts 1101*a* and 1101*b*, connectors 1102*a* and 1102*b*, and wiring lines 1103*a* and 1103*b*, and a garment 1100 on which the fitting member 1106 is fixed.

The number of electrode parts 1101*a* and 1101*b* need only be one or more and is not particularly limited. The positions of the electrode parts 1101*a* and 1101*b* are not particularly limited in the present invention, and can be changed in accordance with the type of bioelectric signal as a detection target. For example, when the detection target is an electrocardiogram waveform, the electrode parts 1101*a* and 1101*b* need only be arranged on the left and right sides of the heart of the living body 1000. When the detection target is a myogenic potential, the two electrode parts 1101*a* and 1101*b* need only be arranged on a target muscle of the living body 1000. The layout and number of electrode parts 1101*a* and 1101*b* do not define the present invention.

The conductive fiber structure forming the electrode parts 1101*a* and 1101*b* is not particularly limited. For example, it is possible to use a textile formed by giving flexibility to a metal such as silver, copper, gold, or stainless steel by processing the metal into thin wiring lines, a material obtained by plating a fiber material with the above-mentioned metal, a carbon fiber, or a material obtained by impregnating a conductive polymer into a fiber material. In particular, a material obtained by using, as a conductive polymer, PEDOT/PSS formed by doping polystyrene sulfonate (poly4-styrene sulfonate; PSS) into poly3,4-ethylenedioxythiophene (PEDOT), and impregnating this conductive polymer into a fiber material, is particularly preferable as the electrode part from the viewpoints of safety and proccessability.

The electrode parts 1101*a* and 1101*b* are fixed on that surface of the fitting member 1106, which comes in contact with the living body 1000. As a method of fixing the electrode parts 1101*a* and 1101*b* to the fitting member 1106, it is desirable to use a method which does not form any hole extending through the obverse and reverse sides of the fitting member 1106, in order to prevent an electrical shortcircuit between the garment 1100 which changes into a conductor when containing an electrolyte, and the electrode parts 1101*a* and 1101*b*. More specifically, it is possible to use, e.g., a method of fixing the electrode parts 1101*a* and 1101*b* by pressing at least portions of their outer circumferences by adhesive tapes, or a method of fixing them by adhesion.

An adhesive to be used to adhere the electrode parts 1101*a* and 1101*b* is not particularly limited, and it is possible to use a resin which is fusible at 100° C. to 180° C. Examples of the resin are polyester, nylon, polyurethane, and their mixtures, but the present invention is not limited to these resins.

As the adhesive tape to be used to fix the electrode parts 1101*a* and 1101*b*, it is possible to use a tape using, as a substrate, a poreless film made of a 10-to 100-µm thick synthetic resin such as polyurethane, polyester, or nylon, a microporous film in which the peripheries of pores are made water-repellent, or a film in which gaps between fibers are filled with a waterproof insulating resin such as polyurethane, polyester, or nylon in advance. A waterproof tape obtained by stacking an adhesive material layer such as a hot melt on at least one surface of this substrate is particularly preferable as the adhesive tape.

As the wiring lines 1103*a* and 1103*b*, it is possible to use a wiring line obtained by printing a conductive resin on the fitting member 1106, a wiring line obtained by adhering a conductive resin film on the fitting member 1106, a wiring line fixed to the fitting member 1106 by pressing, by using an adhesive tape, at least a portion of the outer circumference of each of the wiring lines 1103*a* and 1103*b* formed by a conductive fiber structure, or a wiring line obtained by adhering a conductive fiber structure on the fitting member 1106.

When printing the conductive resin as the wiring lines 1103*a* and 1103*b*, it is possible to fix the electrode parts 1101*a* and 1101*b*, to the fitting member 1106 first and then print the conductive resin so as to obtain electrical connection to the electrode parts 1101*a* and 1101*b*, or print the conductive resin first and then fix the electrode parts 1101*a* and 1101*b* to the fitting member 1106 so as to obtain electrical connection to the conductive resin.

When using the conductive resin film as the wiring lines 1103*a* and 1103*b*, it is possible to fix the electrode parts 1101*a* and 1101*b* to the fitting member 1106 first and then adhere the conductive resin film on the fitting member 1106 so as to obtain electrical connection to the electrode parts 1101*a* and 1101*b*, or adhere the conductive resin film first and then fix the electrode parts 1101*a* and 1101*b* to the fitting member 1106 so as to obtain electrical connection to the conductive resin film.

Likewise, when using the conductive fiber structure as the wiring lines 1103*a* and 1103*b*, it is possible to fix the electrode parts 1101*a* and 1101*b* first and then fix the wiring lines 1103*a* and 1103*b*, or fix the wiring lines 1103*a* and 1103*b* first and then fix the electrode parts 1101*a* and 1101*b*. When using the conductive fiber structure, however, it is also possible to integrally mold the electrode parts 1101*a* and 1101*b* and wiring lines 1103*a* and 1103*b*.

As the adhesive tape to be used to fix the wiring lines 1103*a* and 1103*b*, it is possible to use a tape using, as a substrate, a poreless film made of a synthetic resin such as polyurethane, polyester, or nylon, a microporous film in which the peripheries of pores are made water-repellent, or a film in which gaps between fibers are filled with a waterproof insulating resin such as polyurethane, polyester, or nylon in advance. A waterproof tape obtained by stacking an adhesive material layer such as a hot melt on at least one surface of this substrate is particularly preferable as the adhesive tape.

When the wiring lines 1103*a* and 1103*b* come in contact with the living body 1000, a shunt resistance is inserted into the signal path of a bioelectric signal to be obtained by the electrode parts 1101*a* and 1101*b*, so a desired bioelectric signal to be input to the measurement device attenuates. As shown in FIG. 2, therefore, the wiring lines 1103*a* and 1103*b* are preferably covered with the insulating member in order to prevent contact with the living body 1000. It is also possible to use the above mentioned adhesive tape as the insulating member, thereby simultaneously achieving fixing of the wiring lines 1103*a* and 1103*b* and insulation covering.

In this embodiment, the connectors 1102a and 1102b are fixed to the fitting member 1106 so that conductive parts to be connected to the bioelectric signal measurement device are exposed to the surface which comes in contact with the living body 1000. As the connectors 1102a and 1102b, it is favorable to use a member conventionally used in a detachable part of a garment, such as a metal dot button, conductive zipper, or conductive hook-and-loop fastener, so as not to give any incongruity to the wearer.

In this embodiment, to prevent an electrical shortcircuit between the garment 1100 which changes into a conductor when containing an electrolyte, and the connectors 1102a and 1102b and wiring lines 1103a and 1103b, it is desirable to adopt a method which does not form any hole extending through the obverse and reverse sides of the fitting member 1106, as the method of fixing the connectors 1102a and 1102b. More specifically, when using the conductive hook-and-loop fastener as the connectors 1102a and 1102b, it is possible to use a method of fixing the conductive hook-and-loop fastener by pressing it with an adhesive tape, or a method of fixing it by adhesion. As the adhesive tape to be used to fix the conductive hook-and-loop fastener, the above mentioned waterproof tape is particularly favorable.

On the other hand, this original fixing method cannot be used when using a connector such as a metal dot button which is fixed by caulking the two sides of the button extending through the substrate. Similar to the conductive hook-and-loop fastener, therefore, the connector is fixed by being pressed with an adhesive tape, or fixed by adhesion. Note that when using the metal dot button, it may not be possible to obtain a sufficient fixing strength because the button is smaller than the conductive hook-and-loop fastener in area.

The fitting member 1106 is not particularly limited as long as it is a waterproof electrically insulating member. For example, it is possible to use synthetic resin materials such as polyurethane, polyester, and nylon. However, if the fitting member 1106 is a woven or knitted fabric of a fiber material and exposed to a large amount of water, water is carried as water droplets in gaps between the woven fibers, and the carried water droplets are connected in a row. This may electrically short-circuit the plurality of electrode parts.

Accordingly, the fitting member 1106 is desirably a poreless film made of a resin such as a fluorine resin, polyurethane, polyester, nylon, polyethylene, polypropyrene, or vinyl chloride, a microporous film in which the peripheries of pores are made water-repellent, or a film in which gaps between fibers are filled with a waterproof electrically insulating resin such as polyester or nylon in advance. Also, the fitting member 1106 can be either a member capable of maintaining the electrical insulation properties even when exposed to a large amount of water, or a semipermeable membrane.

The size of the fitting member 1106 need only be a size including the electrode parts 1101a and 1101b, connectors 1102a and 1102b, and wiring lines 1103a and 1103b. However, to prevent electrical connection between the garment 1100 and the conductive parts (the electrode parts 1101a and 1101b, connectors 1102a and 1102b, and wiring lines 1103a and 1103b) of the wearable electrode when water droplets carried on the surface of the fitting member 1106 are connected in a row, the outer edges of the fitting member 1106 desirably extend outward by a distance d or more from the outer edges of the conductive parts of the wearable electrode along the skin surface of the living body 1000, as shown in FIG. 2.

The distance d is a value which must be designed in accordance with the material and surface shape of the fitting member 1106, and does not define the present invention. For example, when using a poreless polyurethane membrane as the fitting member 1106, an intended object can be achieved by setting the distance d at 3 mm or more.

Also, if the waterproof fitting member 1106 touches the skin when the wearer wears the garment 1100, the wearer may feel unpleasantness because sweat is not absorbed. Therefore, the size of the fitting member 1106 is desirably so designed as to meet the above mentioned conditions and to be as small as possible.

Figure 3:
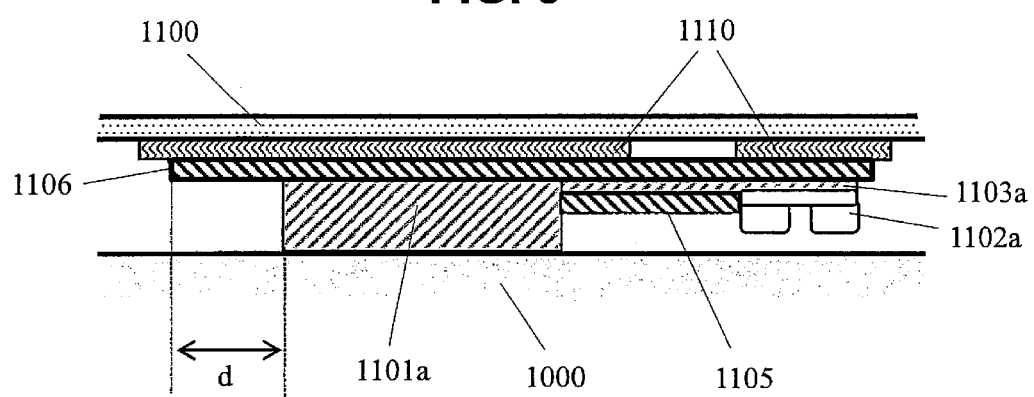
FIG. 3 is a sectional view showing another example of the wearable electrode according to the first embodiment of the present invention.

As the method of fixing the fitting member 1106 on the garment 1100, it is possible to use a method of sewing the outer edges of the fitting member 1106 on the garment 1100, or a method of fixing them by adhesion. When fixing the fitting member 1106 on the garment 1100 by using an adhesive, the adhesive force may decrease depending on a combination of the material (e.g., a blended-spun product of cotton, rayon, and wool) of the garment 1100 and the adhesive, and the fitting member 1106 may be released easily. As shown in FIG. 3, therefore, fixing aid cloth 1110 having an adhesive force larger than that of the garment 1100 with respect to the adhesive is preferably formed between the fitting member 1106 and the garment 1100.

The fixing aid cloth 1110 is one of a woven, knitted, or nonwoven fabric containing at least one of polyester, nylon, acryl, and urethane, and synthetic fibers of polyester, nylon, and the like are particularly preferably usable. The fixing aid cloth 1110 can be fixed by being sewed on the garment 1100. When a material having an adhesive force larger than that of the garment 1100 with respect to the adhesive is used as the fixing aid cloth 1110, a material to be used as the garment 1100 can be selected by taking account of comfortableness and functionality. This makes it possible to obtain the effect of maintaining the release durability against washing and the like, even when the adhesive force between the garment 1100 and the adhesive is small.

The insulating member 1105 is not particularly limited as long as it is a waterproof electrically insulating member, and it is possible to use a synthetic resin material such as polyester or nylon. Similar to the fitting member 1106, if the insulating member 1105 is a woven or knitted fabric of a fiber material and exposed to a large amount of water, water is carried as water droplets in gaps between the woven fibers, and the plurality of electrode parts may electrically short-circuit through ion components contained in the water.

Accordingly, the insulating member 1105 is desirably a poreless film made of a resin such as a fluorine resin, polyurethane, polyester, or nylon, a microporous film in which the peripheries of pores are made water-repellent, or a film in which gaps between fibers are filled with a waterproof electrically insulating resin such as polyester or nylon in advance. Also, the insulating member 1105 can be either a member capable of maintaining the electrical insulation properties even when exposed to a large amount of water, or a semipermeable membrane.

The size of the insulating member 1105 need only be a size including the wiring lines 1103a and 1103b to be electrically insulated. Similar to the fitting member 1106, however, if the waterproof member touches the skin when the wearer wears the garment 1100, the wearer may feel unpleasantness because sweat is not absorbed. Therefore, the insulating member 1105 is desirably as small as possible.

As the method of fixing the insulating member 1105 to the fitting member 1106, it is possible to use a method of sewing the insulating member 1105, or a method of fixing it by adhesion. As described earlier, the use of an adhesive tape as the insulating member 1105 makes it possible to simultaneously achieve fixing of the wiring lines 1103a and 1103b and insulation covering.

The material and shape of the garment 1100 are not particularly limited, and can be changed in accordance with the type of bioelectric signal as a detection target. When obtaining a cardiac potential, for example, a garment shape including a chest part close to the heart of the living body 1000 is desirable. Examples of the shape are a shirt, brassiere, and belly band. When obtaining the myogenic potential of a leg, shapes such as spats, pants, and trousers are desirable. However, the present invention is not limited to these garment shapes. Note that the electrode parts 1101a and 1101b, are desirably brought into tight contact with the skin of the living body 1000 at a pressure of 0.1 kPa (inclusive) to 2.0 kPa (inclusive), and can also be brought into tight contact with the skin by using a belt or the like from outside.

In this embodiment as described above, the electrode parts 1101a and 1101b, connectors 1102a and 1102b, and wiring lines 1103a and 1103b are attached to the waterproof electrically-insulating fitting member 1106, and those portions of the surfaces of the wiring lines 1103a and 1103b, which come in contact with the living body 1000, are covered with the waterproof electrically-insulating member 1105. Even when the garment 1100 gets wet by sweat or the like, therefore, it is possible to prevent a shortcircuit between the living body 1000 and the wiring lines 1103a and 1103b, or a shortcircuit between the plurality of electrode parts 1101a and 1101b, and obtain a desired bioelectric signal.

Also, in this embodiment, the area of the fitting member 1106 is made larger than that of the electrode parts 1101a and 1101b, connectors 1102a and 1102b, and wiring lines 1103a and 1103b, and the outer edges of the fitting member 1106 extend outward by the predetermined distance d or more from the outer edges of the electrode parts 1101a and 1101b, connectors 1102a and 1102b, and wiring lines 1103a and 1103b along the skin surface of the living body 1000. When the garment 1100 gets wet by sweat or the like, therefore, it is possible to prevent a bioelectric signal detected in a portion of the garment 1100 from mixing in a bioelectric signal obtained by the electrode parts 1101a and 1101b.

Note that in this embodiment, the connectors 1102a and 1102b are arranged on that surface of the fitting member 1106, which comes in contact with the living body 1000, so the connectors 1102a and 1102b are desirably covered with an insulating member such that connectors of the bioelectric signal measurement device to be connected to the connectors 1102a and 1102b do not come in contact with the living body 1000.

Second Embodiment

Figure 4:
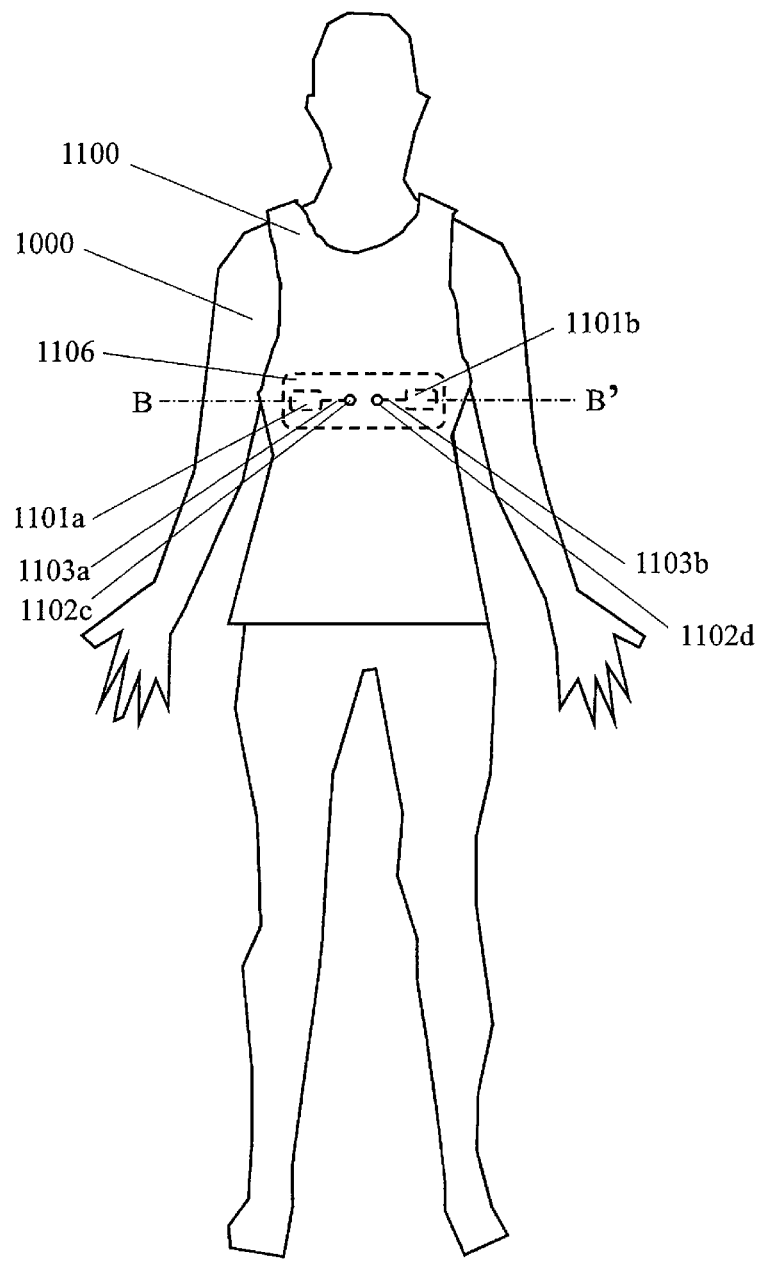
FIG. 4 is a schematic view showing the way a wearable electrode according to the second embodiment of the present invention is worn on a living body.
Figure 5:
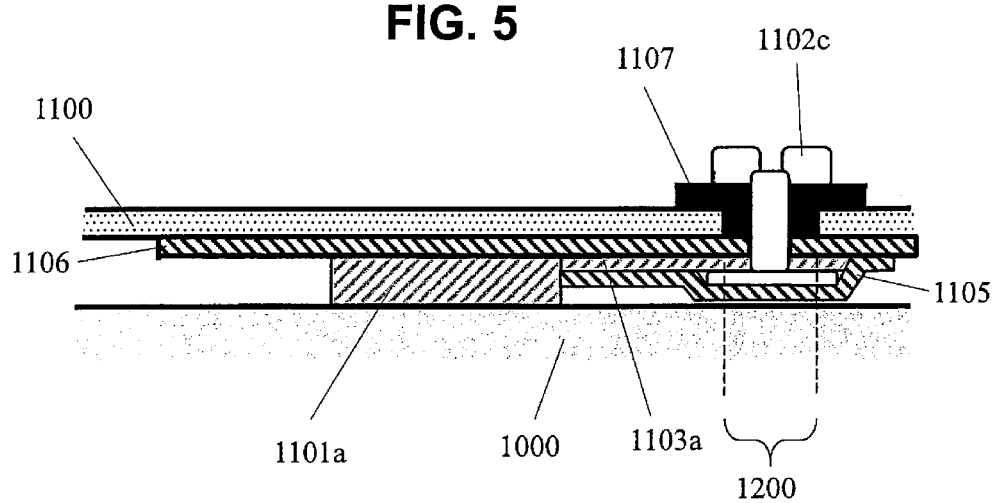
FIG. 5 is a sectional view of the wearable electrode according to the second embodiment of the present invention.

Next, the second embodiment of the present invention will be explained. FIG. 4 is a schematic view showing the way a wearable electrode according to the second embodiment of the present invention is worn on a living body. FIG. 5 is a B-B' sectional view of the wearable electrode shown in FIG. 4. The same reference numerals as in FIGS. 1 and 2 denote the same parts in FIGS. 4 and 5. Note that FIG. 5 shows only a set of an electrode part, wiring line, and connector.

The wearable electrode of this embodiment includes electrode parts 1101a and 1101b, connectors 1102c and 1102d, wiring lines 1103a and 1103b, an insulating member 1105, a fitting member 1106, waterproof electrically-insulating members 1107 for insulation between a garment 1100 and the connectors 1102c and 1102d, and the garment 1100 on which the fitting member 1106 is fixed.

The electrode parts 1101a and 1101b and wiring lines 1103a and 1103b can be the same as those of the first embodiment.

In this embodiment, the connectors 1102c and 1102d are so arranged that conductive parts to be connected to a bioelectric signal measurement device are exposed to a surface opposite to that surface of the garment 1100, which comes in contact with a living body 1000. The material of the connectors 1102c and 1102d is the same as that of the connectors 1102a and 1102b of the first embodiment.

When using the connectors 1102c and 1102d like metal dot buttons which are fixed by caulking the obverse and reverse sides of the buttons extending through a substrate, the waterproof electrically-insulating insulating members 1107 are formed for insulation between at least the surface (the surface opposite to the surface which comes in contact with the living body 1000) of the garment 1100 and the connectors 1102c and 1102d, and insulation between the connectors 1102c and 1102d and the circumferential surfaces of through holes 1200 formed in the garment 1100 in order to form the connectors 1102c and 1102d.

The insulating members 1107 are not particularly limited as long as they are waterproof electrically insulating members, and it is possible to use a synthetic resin material such as polyester or nylon. Like the insulating member 1105, when the insulating members 1107 are a woven or knitted fabric of a fiber material, water is carried in gaps between the woven fibers if the members are exposed to a large amount of water, and the plurality of electrode parts may electrically short-circuit through ion components contained in the water.

Accordingly, the insulating member 1107 is desirably a poreless film made of a resin such as a fluorine resin, polyurethane, polyester, or nylon, a microporous film in which the peripheries of pores are made water-repellent, or a film in which gaps between fibers are filled with a waterproof electrically insulating resin such as polyester or nylon in advance. Also, the insulating member 1107 can be either a member capable of maintaining the electrical insulation properties even when exposed to a large amount of water, or a semipermeable membrane.

Through holes in which the connectors 1102c and 1102d are inserted are formed in the insulating members 1107 beforehand. After the fitting member 1106 is fixed on the garment 1100 and the electrode parts 1101a and 1101b, and wiring lines 1103a and 1103b are fixed to the fitting member 1106, through holes are formed in the garment 1100, fitting member 1106, and wiring lines 1103a and 1103b. In this case, the through hole 1200 formed in at least the garment 1100 is given a diameter larger than that of those portions of the connectors 1102c and 1102d, which penetrate through the garment 1100.

After the insulating members 1107 are inserted into the through holes 1200, the connectors 1102c and 1102d are inserted into the through holes extending through the insulating members 1107, fitting member 1106, and wiring lines 1103a and 1103b, and the obverse and reverse sides of the connectors 1102c and 1102d are caulked. This makes it possible to simultaneously achieve fixing of the connectors 1102c and 1102d and insulating members 1107, insulation covering of the connectors 1102c and 1102d, and electrical connection of the connectors 1102c and 1102d and wiring lines 1103a and 1103b.

It is also possible to install the connectors 1102c and 1102d so as to penetrate through the garment 1100, fitting member 1106, and wiring lines 1103a and 1103b at once in a state in which sheet-like insulating members 1107 are placed on that surface of the garment 1100, which is opposite to the surface which comes in contact with the living body 1000, without forming any through holes in the garment 1100, fitting member 1106, and wiring lines 1103a and 1103b. In this case, a frictional force generated when the connectors 1102c and 1102d are attached pulls the fitting member 1106 and insulating members 1107 into the through holes formed in the garment 1100 when the connectors 1102c and 1102d are attached. This makes it possible to prevent contact between the garment 1100 and the connectors 1102c and 1102d, and implement a structure equal to that shown in FIG. 2.

Figure 6:
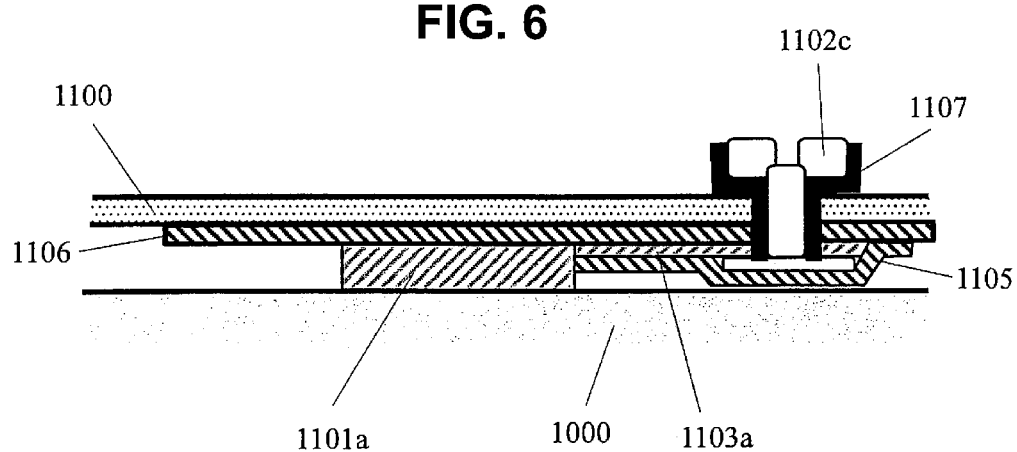
FIG. 6 is a sectional view showing another example of the wearable electrode according to the second embodiment of the present invention.

Furthermore, as shown in FIG. 6, the insulating members 1107 may also be formed in advance on the surfaces of those portions of the connectors 1102c and 1102d, which come in contact with the garment 1100, except for conductive parts to be connected to the bioelectric signal measurement device. In this case, polyester-based, urethane-based, and acrylate-based insulating materials can be used as the insulating members 1107, in addition to the above mentioned materials. Examples of a method of forming the insulating members 1107 are coating and electrodeposition. The step of fixing the insulating members 1107 can be simplified by forming the insulating members 1107 in advance.

Figure 7:
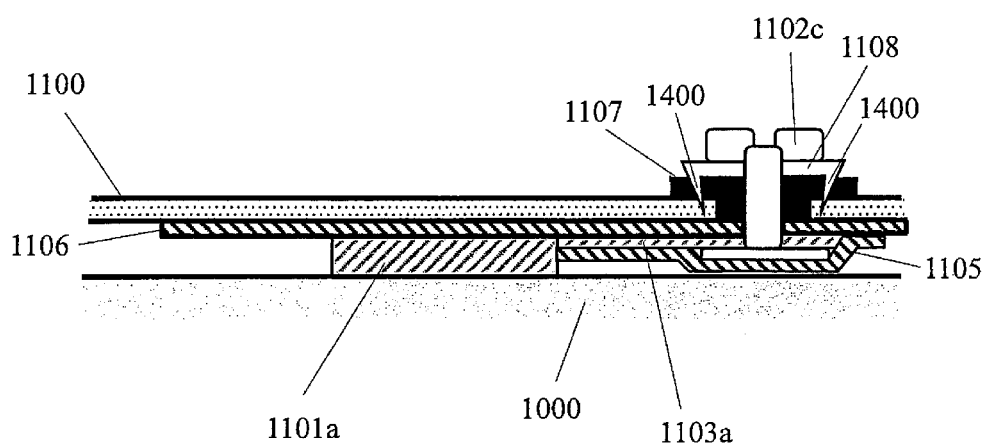
FIG. 7 is a sectional view showing still another example of the wearable electrode according to the second embodiment of the present invention.

When using the connectors 1102c and 1102d like metal dot buttons which are fixed by caulking the obverse and reverse sides of the buttons extending through a substrate, the connectors 1102c and 1102d may be detached from the garment 1100 by a force generated when the bioelectric signal measurement device to be connected to the connectors 1102c and 1102d is detached. As shown in FIG. 7, therefore, a reinforcing member 1108 having a Young's modulus larger than that of the garment 1100 is preferably formed between the connector 1102c or 1102d and the garment 1100.

Examples of a method of fixing the reinforcing member 1108 to the garment 1100 are a method of fixing the reinforcing member 1108 by pressing at least a portion of its outer circumference with an adhesive tape, and a method of fixing it by adhesion. As the adhesive tape to be used to fix the reinforcing member 1108, the above mentioned waterproof tape is particularly favorable. A claw 1400 for hooking the reinforcing member 1108 on the garment 1100 may also be formed on the reinforcing member 1108.

When the reinforcing member 1108 has the claw 1400 and is arranged in contact with the connector 1102c or 1102d, the reinforcing member 1108 is made of a waterproof electrically insulating material. As this material of the reinforcing member 1108, it is possible to use well-known organic resins such as polyethylene, polyvinyl chloride, polystyrene, polypropylene, an acrylic resin, an ABS resin, polyamide, and polycarbonate.

Like the insulating members 1107, though holes into which the connectors 1102c and 1102d are inserted are formed in the reinforcing members 1108 beforehand. In the same manner as above, after the insulating members 1107 are inserted into the through holes 1200 of the garment 1100, the reinforcing members 1108 are fixed to the garment 1100 as described above from above the insulating members 1107. Then, the connectors 1102c and 1102d are inserted into through holes formed in the reinforcing members 1108, insulating members 1107, fitting member 1106, and wiring lines 1103a and 1103b, and the obverse and reverse sides of the connectors 1102c and 1102d are caulked. This makes it possible to simultaneously achieve fixing of the connectors 1102c and 1102d, insulating members 1107, and reinforcing members 1108, reinforcement of fixing of the connectors 1102c and 1102d, insulation covering of the connectors 1102c and 1102d, and electrical connection of the connectors 1102c and 1102d and wiring lines 1103a and 1103b.

Note that the reinforcing member 1108 can also be placed between the insulating member 1107 and the garment 1100. In this case, the reinforcing member 1108 does not come in contact with the connector 1102c or 1102d, so the reinforcing member 1108 can be formed by using a conductive material, and it is possible to use well-known metal materials such as stainless steel, aluminum, and brass. Cloth having a Young's modulus larger than that of the garment 1100 may also be used as the reinforcing member 1108.

The material of the insulating member 1105 is the same as that of the first embodiment. However, when a portion of the connector 1102c or 1102d is exposed to the side which comes in contact with the living body 1000 as shown in FIGS. 5 to 7, that portion of the connector 1102c or 1102d, which comes in contact with the living body 1000, must be covered with the insulating member 1105. When using a metal dot button as each of the connectors 1102c and 1102d, a fitting tool whose side which comes in contact with the living body 1000 is already covered with an insulating resin can be used instead of the insulating member 1105 of the connector part.

The fitting member 1106 and garment 1100 can be the same as those of the first embodiment.

In this embodiment as described above, the electrode parts 1101a and 1101b, and wiring lines 1103a and 1103b are attached to the waterproof electrically-insulating fitting member 1106, and the connectors 1102c and 1102d are attached to the garment 1100. In addition, those portions of the surfaces of the connectors 1102c and 1102d and wiring lines 1103a and 1103b, which come in contact with the living body 1000, are covered with the waterproof electrically-insulating insulating members 1105, and the garment 1100 and the connectors 1102c and 1102d are insulated by the waterproof electrically-insulating insulating members 1107. Even when the garment 1100 gets wet by sweat or the like, therefore, it is possible to prevent a shortcircuit between the living body 1000 and the wiring lines 1103a and 1103b, a shortcircuit between the plurality of electrode parts 1101a and 1101b, or a shortcircuit between the garment 1100 and the connectors 1102c and 1102d, and obtain a desired bioelectric signal. Also, in this embodiment, the connectors 1102c and 1102d are attached to the outside of the garment 1100, so the wearer can easily attach and detach the bioelectric signal measurement device.

Furthermore, in this embodiment, fixing of the connectors 1102c and 1102d can be reinforced by forming the reinforcing members 1108. In this embodiment, even when using a stretchable garment 1100, it is possible to prevent an event in which the connectors 1102c and 1102d are detached from the garment 1100 by the force generated when the bioelectric signal measurement device is disconnected from the connectors 1102c and 1102d, thereby improving the durability of the bioelectrode. In addition, in this embodiment, a stretchable material can be used as the garment 1100, so it is possible to stably bring the electrode parts 1101a and 1101b into contact with the skin of a living body, and stably obtain a desired bioelectric signal for a long time.

Third Embodiment

Figure 8:
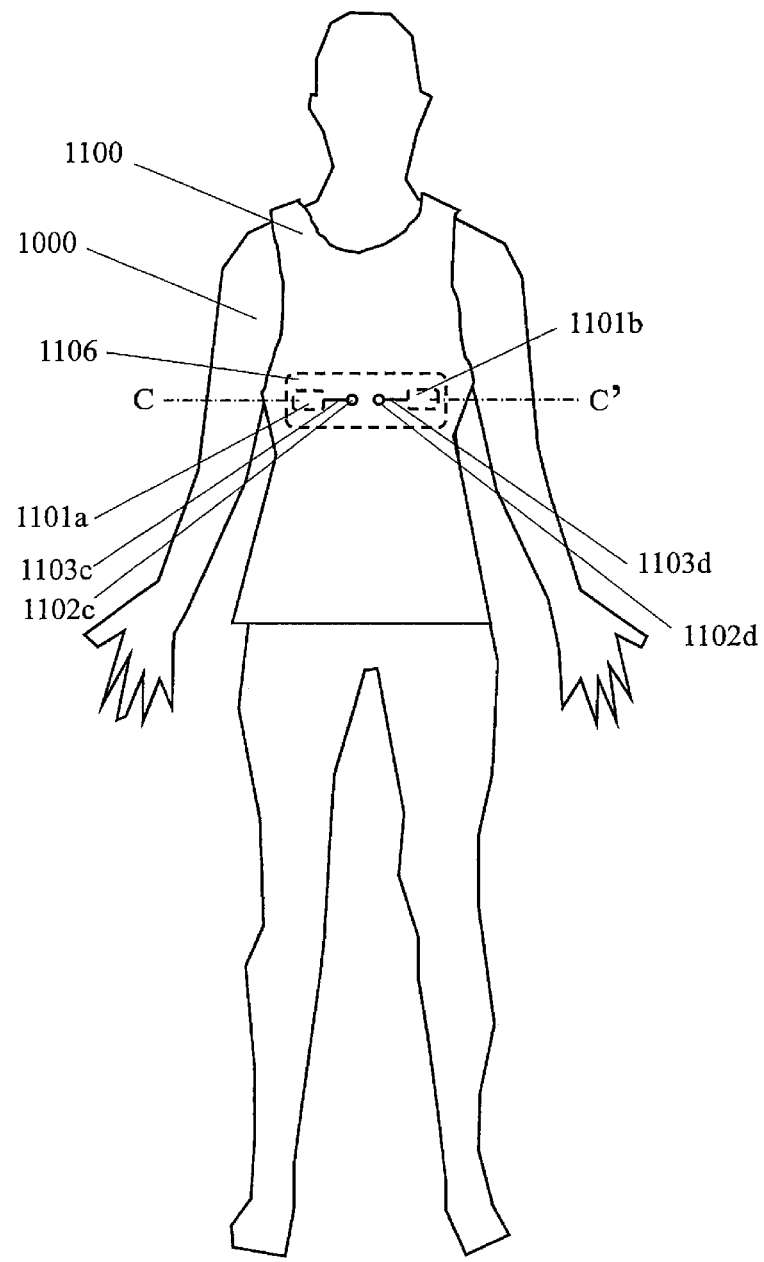
FIG. 8 is a schematic view showing the way a wearable electrode according to the third embodiment of the present invention is worn on a living body.
Figure 9:
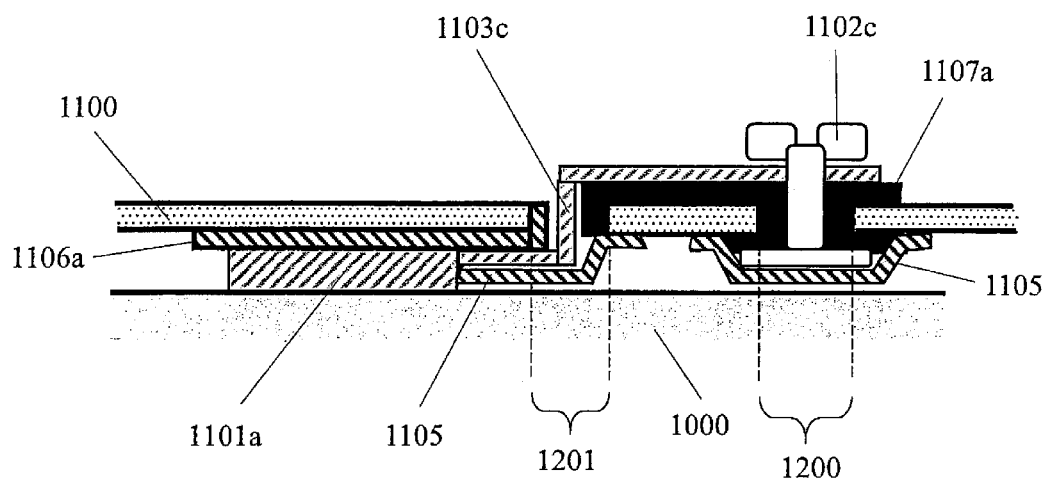
FIG. 9 is a sectional view of the wearable electrode according to the third embodiment of the present invention.

The third embodiment of the present invention will be explained below. FIG. 8 is a schematic view showing the way a wearable electrode according to the third embodiment of the present invention is worn on a living body. FIG. 9 is a C-C' sectional view of the wearable electrode shown in FIG. 8. The same reference numerals as in FIGS. 1 to 7 denote the same parts in FIGS. 8 and 9. Note that FIG. 9 shows only a set of an electrode part, wiring line, and connector.

The wearable electrode of this embodiment includes electrode parts 1101a and 1101b, connectors 1102c and 1102d, wiring lines 1103c and 1103d, insulating members 1105, a fitting member 1106, insulating members 1107a, and a garment 1100.

The electrode parts 1101a and 1101b, can be the same as those of the first and second embodiments.

As in the second embodiment, the connectors 1102c and 1102d are so arranged that conductive parts to be connected to a bioelectric signal measurement device are exposed to that surface of the garment 1100, which is opposite to a surface which comes in contact with the living body 1000.

The material of the wiring lines 1103c and 1103d can be the same as that of the wiring lines 1103a and 1103b of the first and second embodiments. In this embodiment, however, as shown in FIG. 9, the wiring lines 1103c and 1103d are extracted to that side of the garment 1100, which is opposite to the side which comes in contact with the living body 1000, through holes 1201 formed in the garment 1100 between the electrode parts 1101a and 1101b and the connectors 1102c and 1102d.

The size and material of the fitting member 1106a can be the same as those of the fitting member 1106 of the first and second embodiments. However, the fitting member 1106a is formed not only for electrical insulation between that surface of the garment 1100, which comes in contact with the living body 1000, and the wiring lines 1103c and 1103d, but also for electrical insulation between the circumferential surfaces of the through holes 1201 formed in the garment 1100 so as to insert the wiring lines 1103c and 1103d, and the wiring lines 1103c and 1103d. This makes it possible to prevent contact between the garment 1100 and the wiring lines 1103c and 1103d.

The material of the insulating members 1107a can be the same as that of the insulating members 1107 of the first and second embodiments. However, the insulating members 1107a are formed for electrical insulation between at least the surface (the surface opposite to the surface which comes in contact with the living body 1000) of the garment 1100, and the connectors 1102c and 1102d, between the circumferential surfaces of the through holes 1200 formed in the garment 1100 so as to form the connectors 1102c and 1102d, and the connectors 1102c and 1102d, and between the circumferential surfaces of the through holes 1201 formed in the garment 1100 so as to insert the wiring lines 1103c and 1103d, and the wiring lines 1103c and 1103d.

Note that in the example shown in FIG. 9, a portion of the circumferential surface of the through hole 1201, which faces the electrode part 1101a or 1101b, is covered with the fitting member 1106a, and a portion which faces the connector 1102c or 1102d is covered with the insulating member 1107a, but the present invention is not limited to this. Like the through hole 1200, the entire circumferential surface of the through hole 1201 may also be covered with the insulating member 1107a.

In addition, the fitting member 1106a may also cover the both surfaces of the wiring lines 1103c and 1103d.

To attach the connectors 1102c and 1102d, as in the second embodiment, the fitting member 1106a is fixed on the garment 1100, and the electrode parts 1101a and 1101b and wiring lines 1103c and 1103d are fixed to the fitting member 1106a. After that, the wiring lines 1103c and 1103d are extracted through the through holes 1201 to that side of the garment 1100, which is opposite to the side which comes in contact with the living body 1000, and the insulating members 1107a are inserted in the through holes 1200 and 1201 of the garment 1100.

After the wiring lines 1103c and 1103d are arranged on and along the insulating members 1107a, the connectors 1102c and 1102d are inserted into the through holes formed in the wiring lines 1103c and 1103d and insulating members 1107a, and the obverse and reverse sides of the connectors 1102c and 1102d are caulked. This makes it possible to simultaneously achieve fixing of the connectors 1102c and 1102d, wiring lines 1103c and 1103d, and insulating members 1107a, insulation covering of the connectors 1102c and 1102d, and electrical connection of the connectors 1102c and 1102d and wiring lines 1103c and 1103d.

The material of the insulating members 1105 is the same as that of the first embodiment. As in the second embodiment, however, those portions of the connectors 1102c and 1102d, which come in contact with the living body 1000, must be covered with the insulating members 1105.

The garment 1100 can be the same as that of the first embodiment. Note that the fixing aid cloth 1110 explained in the first embodiment may also be applied to the second and third embodiments. Note also that the reinforcing member 1108 explained in the second embodiment may also be applied to the third embodiment.

Fourth Embodiment

The fourth embodiment of the present invention will now be explained. This embodiment shows practical examples of the first embodiment. Note that the present invention is not limited to the following examples.

[Sample 1]

A wearable electrode having the structure shown in FIGS. 1 and 2 was manufactured by using the following members. The electrode parts 1101a and 1101b, were formed by coating, by using a gravure coating method, a circular knitted fabric having a interlock texture of polyester nano-fibers with a dispersant obtained by dispersing 1 wt % of PEDOT/PSS as a conductive component and 5 wt % of an acrylic thermosetting resin as a binder, such that the chemical coating amount was 15 g/m$^2$.

As the garment 1100, spandex plane knit knitted by a 32-gauge circular knitting machine by paralleling an 84 T-36 F polyester false-twisted yawn and 33 T polyurethane elastic yawn was used. As the wiring lines 1103a and 1103b, a ribbon-like material of 110 T-34 of a silver-plated yawn "AGposs" available from MITSUFUJI was used. As the insulating member 1105, a polyurethane waterproof seam tape "αE-110" available from TORAY COATEX was used. As the fitting member 1106, a surface of the same waterproof seam tape as that of the insulating member 1105, which was not an adhesive surface, was coated with a hot-melt adhesive.

[Sample 2]

A wearable electrode having the structure shown in FIG. 3 was manufactured by using the same members as those of above mentioned Sample 1. After the electrode parts 1101a and 1101b, connectors 1102a and 1102b, and wiring lines 1103a and 1103b were attached to the fixing aid cloth 1110 via the fitting member 1106, the fixing aid cloth 1110 is fixed on the garment 1100 by the hot-melt adhesive. The same material as that of the garment 1100 was used as the fixing aid cloth 1110.

[Sample 3]

The same structure as that of above mentioned Sample 2 was manufactured by using, as the garment 1100, spandex plane knit knitted by a 32-gauge circular knitting machine by paralleling a No. 40-count cotton yawn and 33 T polyurethane elastic yawn. The fixing aid cloth 1110 was fixed on the garment 1100 by sewing.

COMPARATIVE EXAMPLE

A wearable electrode was manufactured by using the same members as those of above mentioned Sample 1, and fixing the electrode parts 1101a and 1101b on the garment 1100 by the hot-melt adhesive without using the fitting member 1106.

The wearable electrodes of Samples 1 to 3 and the comparative example were dipped in acidic synthetic sweat for 24 hrs. After that, the electrical resistances of the conductive parts and insulating parts and the electrocardiogram waveforms when the wearable electrodes were worn were measured. Table 1 shows the results.

TABLE 1

|  | Sample 1 | Sample 2 | Sample 3 | Comparative Example |
| --- | --- | --- | --- | --- |
| Conductive part A resistance | 0 Ω | 0 Ω | 0 Ω | 0 Ω |
| Conductive part B resistance | 0 Ω | 0 Ω | 0 Ω | 0 Ω |
| Insulating part A resistance | 22000K Ω | 28000K Ω | 40000K Ω | 100K Ω |
| Insulating part B resistance | 12000K Ω | 18000K Ω | 40000K Ω | 80K Ω |
| Insulating part C resistance | 19000K Ω | 14500K Ω | 40000K Ω | 88K Ω |
| Electrocardiogram waveform | Attenuated by 10% but good | Attenuated by 10% but good | Good | Attenuated by 90% |

"Conductive part A resistance" is the electrical resistance between the electrode part 1101a and the connector 1102a, "conductive part B resistance" is the electrical resistance between the electrode part 1101b, and the connector 1102b, "insulating part A resistance" is the electrical resistance between the electrode parts 1101a and 1101b, "insulating part B resistance" is the electrical resistance between the electrode part 1101a and the garment 1100, and "insulating part C resistance" is the electrical resistance between the electrode part 1101b, and the garment 1100. The numerical values of attenuation in "electrocardiogram waveform" indicate values based on the peak-to-peak amplitude of the electrocardiogram waveform before the wearable electrodes were dipped in the acidic synthetic sweat.

As the synthetic sweat used in measurement, acidic synthetic sweat defined by JIS L 0848 (2004) was prepared as follows. More specifically, this acidic synthetic sweat was prepared by dissolving 0.5 g of L-histidine hydrochloride monohydrate, 5 g of sodium chloride, and 2.2 g of sodium dihydrogen phosphate dihydrate in water, and adding about 15 mL of a 0.1-mol/L sodium hydroxide solution and water to the aqueous solution such that the pH was 5.5 and the overall amount was about 1 L.

Table 1 shows that in the comparative example having the same structure as that of the related wearable electrode, the resistance value of the insulating part decreased, i.e., the function of the insulating part deteriorated, and the electrocardiogram waveform also attenuated by about 90%. By contrast, in Samples 1 to 3 according to the embodiment, the insulating parts maintained the insulation properties, and the electrocardiogram waveforms were good.

INDUSTRIAL APPLICABILITY

The present invention relates to the technique capable of obtaining a desired bioelectric signal even when a garment contains water such as sweat. The present invention is applicable to health management in daily life, grasp of biodata during sports such as jogging and marathon, labor management in construction sites and outdoor works such as road construction and overhead wiring maintenance, and labor management of bus and truck drivers, coal miners, firefighters, and rescue workers.

EXPLANATION OF THE REFERENCE NUMERALS AND SIGNS

1000 . . . living body, 1101a, 1101b, . . . electrode part, 1102a, 1102b, 1102c , 1102d. . . connector, 1103a, 1103b, 1103c, 1103d . . . wiring line, 1105, 1107, 1107a . . . insulating member, 1106, 1106a . . . fitting member, 1108 . . . reinforcing member, 1100 . . . garment, 1110 . . . fixing aid cloth, 1200, 1201 . . . through hole, 1400 . . . claw

The invention claimed is:
1. A bioelectrode comprising:
   a fitting member formed by an electrically insulating member fixed on a surface of a garment that comes in contact with a living body;
   an electrode part formed by a conductive member fixed on a surface of the fitting member that comes in contact with the living body;
   a connector fixed to the fitting member and configured to connect a bioelectric signal measurement device;
   a wiring line fixed to the fitting member and configured to electrically connect the connector and the electrode part, at least a part of the wiring line arranged on and along the surface of the fitting member that comes in contact with the living body; and
   an electrically-insulating first insulating member configured to cover a portion of a surface of the wiring line that comes in contact with the living body.
2. The bioelectrode according to claim 1, wherein the connector is fixed on the surface of the fitting member that comes in contact with the living body.
3. The bioelectrode according to claim 1, further comprising an electrically insulating second insulating member configured to insulate the connector and the garment from each other,
   wherein the connector includes a conductive part configured to connect the bioelectric signal measurement device, the conductive part being exposed to a surface of the garment opposite to the surface that comes in contact with the living body,
   the wiring line couples with the connector on a side of the connector that comes in contact with the living body, and the first insulating member covers respective portions of the surfaces of both the connector and the wiring line that come in contact with the living body.

4. The bioelectrode according to claim 3, further comprising a reinforcing member that has a Young's modulus larger than that of a material of the garment,
wherein the connector is fixed to the garment by being penetrated through the garment, and
the reinforcing member is fixed to the garment in a state in which the connector penetrates through a hole formed in the reinforcing member along a thickness direction of the reinforcing member and a hole formed in the garment along a thickness direction of the garment.

5. The bioelectrode according to claim 3, wherein the second insulating member is formed on a surface of a portion of the connector that comes in contact with the garment.

6. The bioelectrode according to claim 1, further comprising an electrically insulating second insulating member configured to insulate the connector and the garment from each other, and insulate the wiring line and the garment from each other,
wherein the connector includes a conductive part configured to connect the bioelectric signal measurement device, the conductive part being exposed on a surface of the garment opposite to the surface that comes in contact with the living body,
the wiring line is arranged through a through hole formed in the garment, and couples with the connector on a side of the garment opposite to the side that comes in contact with the living body, and
the first insulating member covers respective portions of the surfaces of both the connector and the wiring line that come in contact with the living body.

7. The bioelectrode according to claim 6, further comprising a reinforcing member that has a Young's modulus larger than that of a material of the garment,
wherein the connector is fixed to the garment by being penetrated through an inside and an outside of the garment, and
the reinforcing member is fixed to the garment in a state in which the connector penetrates through a hole formed in the reinforcing member along a thickness direction of the reinforcing member and a hole formed in the garment along a thickness direction of the garment.

8. The bioelectrode according to claim 6, wherein the second insulating member is formed on a surface of a portion of the connector that comes in contact with the garment.

9. The bioelectrode according to claim 6, wherein the second insulating member is arranged on the surface of the garment opposite to the one that comes contact with the living body, and
the wiring line includes another part arranged on and along the surface of the second insulating member opposite to the one that comes contact with the garment.

10. The bioelectrode according to claim 1, further comprising a fixing aid cloth formed between the fitting member and the garment.

11. The bioelectrode according to claim 10, further comprising an adhesive fixing the fixing aid cloth to the garment, wherein the fixing aid cloth is one of a woven fabric, a knitted fabric, and a nonwoven fabric containing at least one of polyester, nylon, acryl, and urethane, and an adhesive force between the fixing aid cloth and the adhesive is larger than that between the garment and the adhesive.

* * * * *